(12) United States Patent
Fukae

(10) Patent No.: US 7,955,819 B2
(45) Date of Patent: Jun. 7, 2011

(54) PROCESS FOR PRODUCING SUGAR CHAIN ASPARAGINE DERIVATIVE

(75) Inventor: Kazuhiro Fukae, Tokushima (JP)

(73) Assignee: Otsuka Chemical Holdings Co., Ltd., Chuo-ku, Osaka (JP)

( * ) Notice: Subject to any disclaimer, the term of this patent is extended or adjusted under 35 U.S.C. 154(b) by 476 days.

(21) Appl. No.: 10/544,212

(22) PCT Filed: Feb. 3, 2004

(86) PCT No.: PCT/JP2004/001048
§ 371 (c)(1),
(2), (4) Date: Aug. 2, 2005

(87) PCT Pub. No.: WO2004/070046
PCT Pub. Date: Aug. 19, 2004

(65) Prior Publication Data
US 2006/0205039 A1    Sep. 14, 2006

(30) Foreign Application Priority Data

Feb. 4, 2003  (JP) ................................ 2003-026609

(51) Int. Cl.
*C12P 1/00* (2006.01)
(52) U.S. Cl. ........ 435/41; 435/68.1; 435/85; 435/91.53; 435/101; 536/1.11; 536/17.2; 536/127
(58) Field of Classification Search .................. None
See application file for complete search history.

(56) References Cited

U.S. PATENT DOCUMENTS

| 5,834,423 | A | 11/1998 | Koketsu et al. ............ 514/7 |
| 2004/0181054 | A1 | 9/2004 | Kajihara et al. ......... 536/123.13 |

FOREIGN PATENT DOCUMENTS

| JP | 08099988 A | * | 4/1996 |
| WO | 03/008431 A1 | | 1/2003 |

OTHER PUBLICATIONS

Koketsu et al., The journal of Food Science, 1993, vol. 58, No. 4, p. 743-747.*
Yamamoto, K., Journal of Bioscience and Bioengineering, 2001, vol. 92, No. 6, p. 493-501.*
Stedman's Medical Dictionary 27th Edition.*
Narahashi et al., Journal of Biochemistry, 1967, vol. 62, No. 6, Abstract.*
Koketsu et al., J. Carbohydrate Chemistry, 1995, vol. 14, No. 6, p. 833-841.*
Koketsu et al. (The journal of Food Science, 1993, vol. 58, No. 4, p. 743-747.*
SCORE search results pp. 1-2.*
Yamamoto, K. (Journal of Bioscience and Bioengineering, 2001, vol. 92, No. 6, p. 493-501.*
Inazu Toshiyuki et al., "Preparation of Fmoc-asparagine Derivatives Having Natural N-linked Oligosaccharide, and its Application to the Synthesis of Glycopeptides", *Peptide Science*, 1999, vol. 1998, pp. 153-156.
Inazu, Toshiyuki, et. al., "Preparation of Fmoc-asparagine Derivatives Having Natural N-Linked Oligosaccharide, and Its Application to the Synthesis of Glycopeptides"; Peptide Science 1998: M. Kondo (Ed.), Protein Research Foundation, Osaka (1999); pp. 153-156.
Koketsu, Mamoru, et. al., "Sialyloligosaccharides of Delipidated Egg Yolk Fraction"; Journal of Food Science, vol. 58, No. 4 (1993); pp. 743-747.
Yamamoto, Kenji; "Chemo-Enzymatic Synthesis of Bioactive Glycopeptide Using Microbial Endoglycosidase"; Journal of Bioscience and Bioengineering, vol. 92, No. 6 (2001); pp. 493-501.
Seko, Akira. et al., "Occurrence of a sialylglycopeptide and free sialylglycans in hen's egg yolk", *Biochemica et Biophysica Acta*, vol. 1335, (1997) pp. 23-32.
Lin, Chun-Hung, et al., "Enzymatic Synthesis of a Sialyl Lewis X Dimer from Egg Yolk as an Inhibitor of E-Selectin"; Biorganic & Medicinal Chemistry, vol. 3, No. 12 (1995); pp. 1625-1630.

* cited by examiner

*Primary Examiner* — Kade Ariani
(74) *Attorney, Agent, or Firm* — Osha • Liang LLP

(57) ABSTRACT

A process for preparing asparagine-linked oligosaccharide derivatives including the steps of: (a) treating a delipidated egg yolk with a protease to obtain a mixture of peptide-linked oligosaccharides, (b) treating the mixture of peptide-linked oligosaccharides with a peptidase to obtain a mixture of asparagine-linked oligosaccharides, (c) introducing a lipophilic protective group into the asparagine-linked oligosaccharides in the mixture to obtain a mixture of asparagine-linked oligosaccharide derivatives, and (d) subjecting the mixture of asparagine-linked oligosaccharide derivatives to chromatography to separate the mixture into individual asparagine-linked oligosaccharide derivatives.

7 Claims, No Drawings

PROCESS FOR PRODUCING SUGAR CHAIN ASPARAGINE DERIVATIVE

This application is a 371 of international application PCT/JP2004/001048, which claims priority based on Japanese patent application No. 2003-26609 filed Feb. 4, 2003, which is incorporated herein by reference.

TECHNICAL FIELD

The present invention relates to a process for preparing asparagine-linked oligosaccharides.

BACKGROUND ART

In recent years, molecules of oligosaccharides have attracted attention as third chain life molecules following nucleic acids (DNA) and proteins. The human body is a huge cell society comprising about 60 trillion cells, and the surfaces of all the cells are covered with oligosaccharide molecules. For example, ABO blood groups are determined according to the difference of oligosaccharides over the surfaces of cells.

Oligosaccharides function in connection with the recognition of cells and interaction of cells and are key substances for the establishment of the cell society. Disturbances in the cell society lead, for example, to cancers, chronic diseases, infectious diseases and aging.

For example, it is known that when cells cancerate, changes occur in the structure of oligosaccharides. It is also known that *Vibrio cholerae*, influenza virus, etc. ingress into cells and cause infection by recognizing and attaching to a specific oligosaccharide.

Oligosaccharides are much more complex than DNA or proteins in structure because of the diversity of arrangements of monosaccharides, modes or sites of linkages, lengths of chains, modes of branches and overall structures of higher order. Accordingly, biological information derived from the structures thereof is more diversified than is the case with DNA and proteins. Although the importance of research on oligosaccharides has been recognized, the complexity and variety of structures thereof have delayed progress in the research on oligosaccharides unlike the studies on DNA and proteins.

On the other hand, it is known that asparagine-linked oligosaccharides are obtained from delipidated egg yolk (see, for example, Patent Literature 1). According to Patent Literature 1, asparagine-linked oligosaccharides are obtained in larger quantities than conventionally by adding almond or apricot seed to delipidated egg yolk. However, this process provides asparagine-linked oligosaccharides which are 95% or 92% in purity, failing to isolate pure asparagine-linked oligosaccharides. As to the yield, 100 kg of delipidated egg yolk affords 29.5 g or 27.2 g of a disialyloligosacchride (disialylundecasaccharide).

It is also known that a glycopeptide (SGP: sialylglycopeptide) extracted from a soluble fraction of chicken eggs affords asparagine-linked oligosaccharides. The SGP is a compound wherein an asparagine moiety of a peptide chain comprising six moieties of amino acids is linked to the reducing terminal of a composite oligosaccharide comprising eleven sugar moieties. However, the process of Seko et. al [Biochemica Biophysica Acta, Vol. 1335, p. 23(1997)], for example, yielded only about 8 mg of SGP from one chicken egg yolk.

[Patent Literature 1] WO96/02255 (claims 8 and 10)

An object of the present invention is to provide a process for preparing asparagine-linked oligosaccharide derivatives by which various isolated asparagine-linked oligosaccharide derivatives can be obtained in larger quantities and with much greater ease than conventionally for use in the field of developing pharmaceuticals or the like.

DISCLOSURE OF THE INVENTION

The present invention provides an invention of following features.

1. A process for preparing asparagine-linked oligosaccharide derivatives including the steps of: (a) treating a delipidated egg yolk with a protease to obtain a mixture of peptide-linked oligosaccharides, (b) treating the mixture of peptide-linked oligosaccharides with a peptidase to obtain a mixture of asparagine-linked oligosaccharides, (c) introducing a lipophilic protective group into the asparagine-linked oligosaccharides in the mixture to obtain a mixture of asparagine-linked oligosaccharide derivatives, and (d) subjecting the mixture of asparagine-linked oligosaccharide derivatives to chromatography to separate the mixture into individual asparagine-linked oligosaccharide derivatives.

2. The process described above for preparing asparagine-linked oligosaccharide derivatives wherein the delipidated egg yolk is obtained by delipidating an avian egg yolk with an organic solvent.

3. The process described above for preparing asparagine-linked oligosaccharide derivatives wherein the asparagine-linked oligosaccharide derivatives are asparagine-linked undeca- to penta-saccharide derivatives.

4. The process described above for preparing asparagine-linked oligosaccharide derivatives wherein the lipophilic protective group is a carbonate-containing group, acyl group, allyl group, Fmoc group or Boc group.

5. The process described above for preparing asparagine-linked oligosaccharide derivatives wherein the asparagine-linked oligosaccharides contained in the mixture of asparagine-linked oligosaccharides obtained by the step (b) are hydrolyzed before the subsequent step to cut off some sugar moieties.

6. The process described above for preparing asparagine-linked oligosaccharide derivatives wherein the asparagine-linked oligosaccharide derivatives contained in the mixture of asparagine-linked oligosaccharide derivatives obtained by the step (c) are hydrolyzed before the subsequent step to cut off some sugar moieties.

The process of the invention for preparing asparagine-linked oligosaccharide derivatives is distinctly characterized by treating a delipidated egg yolk obtained from an egg yolk, for example, from an avian egg yolk, with a protease to obtain a mixture of peptide-linked oligosaccharides, then treating the mixture with a peptidase to obtain a mixture of asparagine-linked oligosaccharides, subsequently introducing (for bonding) a lipophilic protective group into the asparagine-linked oligosaccharides in the mixture to obtain a mixture of asparagine-linked oligosaccharide derivatives, and thereafter separating the mixture into individual asparagine-linked oligosaccharide derivatives. The term an "asparagine-linked oligosaccharide" as used herein refers to an oligosaccharide having asparagine linked thereto. Further the term "oligosaccharides capable of linking to asparagine" refers to a group of oligosaccharides wherein N-acetylglucosamine present at a reducing terminal is attached by N-glucoside linkage to the acid amino group of asparagine (Asn) in the polypeptide of a protein and which has Man($\beta$1-4)GlcNac($\beta$1-4)GlcNac as the core structure. The term an "asparagine-linked oligosaccharide derivative" refers to an asparagine-linked oligosaccharide wherein a lipophilic protective group is attached to asparagine moiety. Further "AcHN" in the structural formulae of compounds refers to an acetamido group.

Stated more specifically, the process of the invention for producing asparagine-linked oligosaccharide derivatives include:

(a) the step of preparing a mixture of peptide-linked oligosaccharides from a delipidated egg yolk using a protease, (b) the step of preparing a mixture of asparagine-linked oligosaccharides from the mixture of peptide-linked oligosaccharides using a peptidase, (c) the step of introducing a lipophilic protective group into the asparagine-linked oligosaccharides in the mixture to obtain a mixture of asparagine-linked oligosaccharide derivatives, and (d) the step of subjecting the mixture of asparagine-linked oligosaccharide derivatives to chromatography to separate the mixture into individual asparagine-linked oligosaccharide derivatives.

The process of the invention for preparing asparagine-linked oligosaccharide derivatives from delipidated egg yolk will be described below in detail.

The delipidated egg yolk to be used in the present invention is not limited particularly. For example, a delipidated egg yolk obtained by delipidating with organic solvent? an avian egg yolk is desirable. (Examples of desirable avian egg yolks are those of chickens, quails, ducks, wild ducks, doves, etc. Especially desirable is the egg yolk of chickens in view of the amount of human-type asparagine-linked oligosaccharides, particularly of human-type 2-branched asparagine-linked oligosaccharides, contained in the egg yolk.) Examples of preferred organic solvents are methanol, ethanol, diethyl ether, etc.

In the step (a), proteins are cut off from the delipidated egg yolk with a protease to obtain a mixture of peptide-linked oligosaccharides (asparagine-linked oligosaccharide peptides) contained in the delipidated egg yolk. The protease to be used in this step are those generally available such as Pronase (product of Wako Pure Chemical Industries, Ltd.) and Orientase (product of Hankyu Bioindustry Co., Ltd.).

It is desirable to remove the components other than peptide-linked oligosaccharides from the mixture of peptide-linked oligosaccharides by a known method, for example, by various chromatographic procedures using a gel filtration column, ion exchange column or the like or a purification method using high performance liquid chromatography (HPLC).

In the step (b), the peptides of peptide-linked oligosaccharides obtained in the step (a) are decomposed with a peptidase to obtain a mixture of asparagine-linked oligosaccharides contained in the peptide-linked oligosaccharides. Examples of useful peptidases are those commonly available such as actinase.

It is desirable to remove the components other than asparagine-linked oligosaccharides from the mixture of asparagine-linked oligosaccharides by a known method, for example, by various chromatographic procedures using a gel filtrarion column, ion exchange column or the like or a purification method using high performance liquid chromatography (HPLC).

Further from the viewpoint of efficiently obtaining asparagine-linked oligosaccharide derivatives having the desired oligosaccharide structure, it is desirable to hydrolyze the asparagine-linked oligosaccharides contained in the mixture and to cut off some sugar moieties before performing the following step. Useful methods of hydrolysis include a method wherein an acid is used, and a method wherein an enzyme is used.

The acid to be used is not limited specifically; useful examples are inorganic acids and organic acids such as hydrochloric acid, sulfuric acid, nitric acid and trifluoroacetic acid, cation exchange resins, insoluble solid reagents (such as silica gel), etc. Examples of useful enzymes are glycosidase which can be of either of the endo-type and exo-type as to the reaction mode of the enzyme. Such an enzyme is not limited particularly; commercial enzymes, enzymes isolated anew and those created by genetic engineering techniques are useful insofar as they have the desired activity.

The enzymatic reaction can be carried out under known conditions. The progress of the reaction may be monitored by thin-layer chromatography to terminate the reaction at the stage where the contemplated compound is available in the largest quantity.

In the step (c), a lipophilic protective group is introduced into the asparagine-linked oligosaccharides contained in the mixture resulting from the step (b).

The protecting group is not particularly limited, and there can be used, for instance, a carbonate-containing group such as 9-fluorenylmethoxycarbonyl (Fmoc) group, t-butyloxycarbonyl (Boc) group or allyloxycarbonate (Alloc) group, acyl group such as acetyl (Ac) group, allyl group or benzyl group. In considering synthesis efficiency and isolation/purification efficiency in a subsequent step, the above protecting group is preferably a carbonate-containing group such as 9-fluorenylmethoxycarbonyl (Fmoc) group, t-butyloxycarbonyl (Boc) group or allyloxycarbonate group and acyl group such as acetyl group. From the viewpoint that the resulting asparagine-linked oligosaccharide derivative can be immediately used in the synthesis of a desired glycopeptide, the above protecting group is preferably Fmoc group and Boc group which are widely used in peptide synthesis. The Fmoc group is especially effective when there exists in the oligosaccharide a sugar, such as sialic acid, which is relative unstable under acidic conditions. The introduction of the protecting group may be carried out according to a known process (for instance, Protecting Groups in Organic Chemistry, John Wiley & Sons INC., New York 1991, ISBN 0-471-62301-6).

For instance, when Fmoc group is used, an appropriate amount of acetone or DMF is added to the mixture containing asparagine-linked oligosaccharides, 9-fluorenylmethyl-N-succinimidyl carbonate and sodium hydrogencarbonate are further added thereto and dissolved, and thereafter the resulting mixture is subjected to a binding reaction of Fmoc group to an asparagine moiety at 25° C., whereby the Fmoc group can be introduced into the asparagine moiety of the above asparagine-linked oligosaccharide.

According to the procedures described above, asparagine-linked oligosaccharide derivatives into which a lipophilic protecting group is introduced are obtained.

In the step (d), the mixture of asparagine-linked oligosaccharide derivatives obtained by the step (c) is separated into individual asparagine-linked oligosaccharide derivatives by known chromatography, especially by fractionating chromatography. The mixture of asparagine-linked oligosaccharide derivatives obtained is usable directly in this step, whereas from the viewpoint of obtaining asparagine-linked oligosaccharide derivatives having the desired oligosaccharide structure efficiently, the asparagine-linked oligosaccharide derivatives contained in the mixture may be hydrolyzed before this step to cut off some sugar moieties and to use the resulting mixture of asparagine-linked oligosaccharide derivatives. The extent of sugar residues to be cut off is the same as in the previous case. The hydrolysis can be conducted in the same manner as above.

The separation of each of asparagine-linked oligosaccharide derivatives by chromatography can be carried out by appropriately using known chromatographies, singly or in a combination of plural chromatographies.

For instance, the resulting mixture of asparagine-linked oligosaccharide derivatives is purified by a gel filtration column chromatography, and then purified by using HPLC. The column which can be used in HPLC is preferably a reverse phase column, for instance, ODS, phenyl-based, nitrile-based, or anion exchange-based column, and concretely, a mono Q column manufactured by Pharmacia, Iatro-beads column manufactured by Iatron can be utilized. The separation conditions and the like may be adjusted by referring to a known condition. According to the above procedures, each of the desired asparagine-linked oligosaccharide derivatives can be obtained from the mixture of asparagine-linked oligosaccharide derivatives.

Examples of asparagine-linked oligosaccharide derivatives prepared by the above process are asparagine-linked undeca- to penta-saccharide derivatives, preferably asparagine-linked undeca- to hepta-saccharide derivatives, more preferably asparagine-linked undeca- to nona-saccharide derivatives. The most preferable is asparagine-linked undecasaccharide derivative of the following formula wherein Prot is a protective group.

sis is carried out with a glycosidase of which cleavage mode of the oligosaccharide moieties is clear, from the viewpoint of more efficiently obtaining the asparagine-linked oligosaccharide derivatives having the desired oligosaccharide structures.

As described above, each of the various asparagine-linked oligosaccharide derivatives of which branching structures at the terminals of the oligosaccharides are not uniform, can be obtained as individual isolated compounds by further hydrolyzing the derivatives with various glycosidases and the like to remove the sugar moieties at non-reducing terminals of the oligosaccharides after the obtainment of each of the asparagine-linked oligosaccharide derivatives. Moreover, even a larger number of the kinds of the asparagine-linked oligosaccharide derivatives can be prepared by changing the order or the kind of hydrolysis with various glycosidases.

The present invention further provides a process for preparing various isolated asparagine-linked oligosaccharides in large quantities. This process includes, subsequently to the step of preparing asparagine-linked oligosaccharide derivative or derivatives of the foregoing process for preparing such derivative, the step of removing the protective group from the resulting asparagine-linked oligosaccharide derivative or derivatives.

The removal of the protecting group from the asparagine-linked oligosaccharide derivative can be carried out in accor-

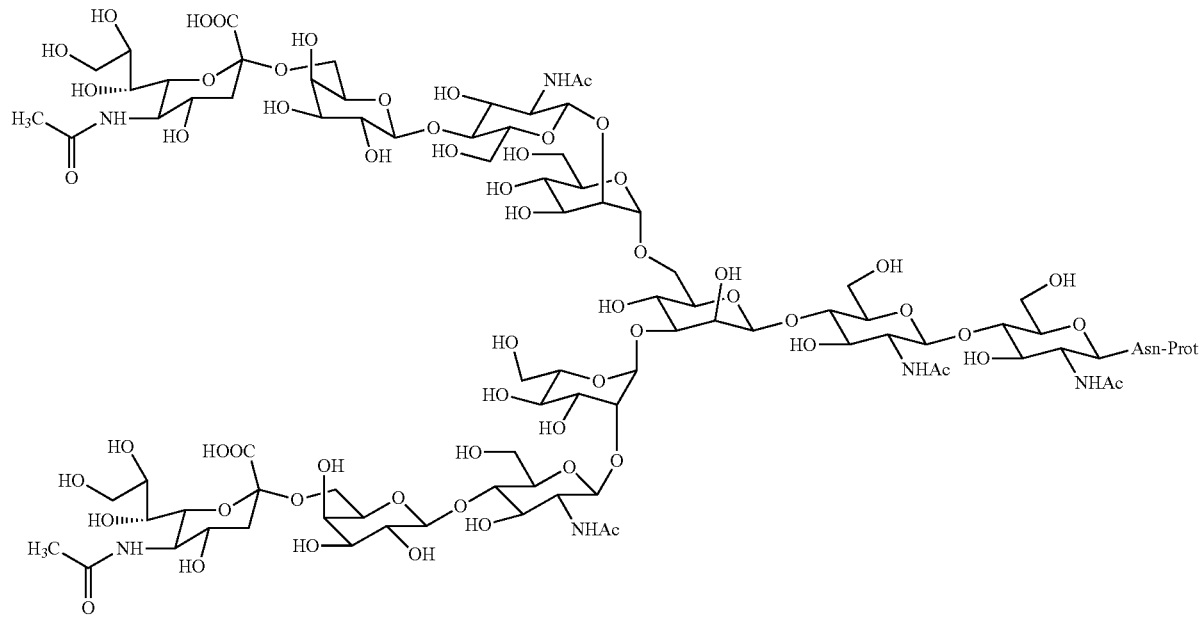

Furthermore, the asparagine-linked oligosaccharide derivative having a desired oligosaccharide structure can be efficiently obtained by hydrolyzing the asparagine-linked oligosaccharide derivatives separated in the above step. For instance, in the stage of separating the asparagine-linked oligosaccharide derivatives, the asparagine-linked oligosaccharide derivatives can be roughly separated by limiting the kinds of the asparagine-linked oligosaccharide derivatives contained in the mixture, and thereafter the asparagine-linked oligosaccharide derivatives are subjected to hydrolysis, for instance, hydrolysis with a glycosidase, whereby the asparagine-linked oligosaccharide derivatives having the desired oligosaccharide structures can be efficiently obtained. Here, the hydrolysis can be carried out in the same manner as described above. Especially, it is preferable that the hydrolysis dance with a known process (for instance, see Protecting Groups in Organic Chemistry, John Wiley & Sons INC., New York 1991, ISBN 0-471-62301-6). For instance, when the protecting group is Fmoc group, the Fmoc group can be removed by adding morpholine to the asparagine-linked oligosaccharide derivative in N,N-dimethylformamide (DMF) to carry out the reaction. On the other hand, Boc group can be removed by a reaction with a weak acid. After the removal of the protecting group, an asparagine-linked oligosaccharide may be properly obtained by purifying a reaction mixture by a known process such as various chromatographies employing a gel filtration column, an ion exchange column or the like or a process of separation by HPLC as desired.

In case the protecting group is a benzyl group, the removal of the benzyl group from the asparagine-linked oligosaccharide derivative can be carried out in accordance with a known process (for instance, see Protecting Groups in Organic Chemistry, John Wiley & Sons INC., New York 1991, ISBN 0-471-62301-6).

Further, the removal of the asparagine moiety from the asparagine-linked oligosaccharide can be carried out in accordance with a known process. For instance, the asparagine-linked oligosaccharide is reacted with anhydrous hydrazine and then acetylated to remove the asparagine moiety, whereby oligosaccharide can be obtained. Also, oligosaccharide can be also obtained by refluxing the asparagine-linked oligosaccharide with heating in a basic aqueous solution and thereafter acetylating the asparagine-linked oligosaccharide to remove the asparagine moiety. After the removal of the asparagine moiety, the oligosaccharide may be purified appropriately by a known process such as various chromatographies employing a gel filtration column, an ion exchange column or the like, and a separation process by HPLC as desired.

As described above, according to the present invention, the asparagine-linked oligosaccharide derivative, the asparagine-linked oligosaccharide and the oligosaccharide (hereinafter these three terms are collectively referred to as "oligosaccharide series" in some case) each having a desired oligosaccharide structure can be prepared at a low cost, efficiently and in a large amount.

The oligosaccharide series of the invention are very useful in the field of development of pharmaceuticals. For example, vaccines for cancers are an example of application to the development of drugs. It is known that cells cancerate produce an oligosaccharide which is not found in the living body. It is also known that when chemically prepared and given to the human body as a vaccine, such an oligosaccharide inhibits the growth of cancer. If the desired oligosaccharide series can be produced according to the invention, it is possible to prepare a vaccine which is effective for treating cancer. The oligosaccharide series obtained by the invention can further be made into derivatives by attaching novel sugar moieties thereto through combinations of chemical reactions and reactions of sugar transferases for the preparation of novel vaccines.

While for example, erythropoietin (EPO) which is a glycoprotein is used as a drug for treating anemia because of the ability thereof to proliferate erythrocytes, it has been found that EPO fails to exhibit activity when having no oligosaccharide bonded thereto. Thus, proteins include those exhibiting physiological activity when having an oligosaccharide bonded thereto, so that it is possible to prepare a protein in a large quantity by an $E.$ $coli$ expression system which is incapable of bonding oligosaccharides to the protein, and subsequently introducing an oligosaccharide prepared by the invention and having a desired structure into the protein for causing the protein to exhibit a physiological activity. Alternatively, a novel glycoprotein having novel physiological activity can be synthesized by introducing oligosaccharides prepared by the invention and having various structures into a desired protein.

Furthermore, oligosaccharides present in natural glycoproteins can be replaced with oligosaccharides prepared by the invention to thereby give novel physiological activity to the glycoprotein. Useful as a technique for replacing the oligosaccharide present in glycoproteins by the oligosaccharide obtained by the invention is, for example, the process disclosed in P. Sears and C. H. Wong, Science, 2001, vol. 291, pp. 2344-2350. With this process, the glycoprotein is treated with β-N-acetylglucosaminidase (Endo-H) so as to permit only one N-acetylglucosamine moiety to remain bonded to the asparagine moiety on the surface of the glycoprotein. Subsequently, a desired oligosaccharide in the asparagine-linked oligosaccharide obtained by the invention is bonded to the N-acetylglucosamine moiety using β-N-acetylglucosaminidase (Endo-M). It is also possible to prepare a glycoprotein having N-acetylglucosamine moiety utilizing an $E.$ $coli$ expression system and using tRNA having N-acetylglucosamine bonded thereto, and to thereafter introduce a desired oligosaccharide in the asparagine-linked oligosaccharide obtained according to the invention into the glycoprotein with use of Endo-M.

Presently, the use of glycoproteins as therapeutic drugs involves the problem that the glycoprotein administered is metabolized at a high rate because when sialic acid is removed from the oligosaccharide terminal of the glycoprotein in vivo, the glycoprotein is metabolized immediately in the liver. For this reason, there is a need to give the glycoprotein in a considerable amount. It is therefore possible to control the rate of metabolism in the living body and to decrease the dose of glycoprotein to be given by preparing an oligosaccharide according to the invention, with sialic acid which is difficult to remove incorporated therein at its terminal, and introducing the oligosaccharide into the contemplated glycoprotein with use of Endo-M.

BEST MODE OF CARRYING OUT THE INVENTION

The present invention will be further described with reference to the following examples, but the invention is in no way limited to these examples.

EXAMPLE 1

One egg yolk was placed as broken into 67 ml of ethanol (EtOH) being stirred. The mixture was stirred for about 5 hours and then filtered, followed by washing with 30 ml of EtOH. To the resulting crystals was added 83 ml of EtOH again, and the mixture was stirred overnight. The mixture was thereafter filtered, followed by washing with 30 ml of EtOH. The crystals obtained were dried, giving about 3 g of delipidated egg yolk.

(a) The delipidated egg yolk was dissolved in a phosphate buffer (7.0 in pH, 30 ml), and $NaN_3$ (10 mg) was added to the solution. Orientase ONS (product of Hankyu Bioindustry Co., Ltd., 1.0 g) was further added to the solution, and the mixture was allowed to stand at 50° C. for about 24 hours. After the termination of the reaction was confirmed by TLC, the reaction mixture was filtered with Celite. The filtrate was concentrated and purified by gel filtration column chromatography (Sephadex G-25, 2.5×100 cm, $H_2O$). The fractions containing the desired saccharides were collected, concentrated and then freeze-dried.

(b) To the residue (about 430 mg) obtained were added Tris-hydrochloric acid.calcium chloride buffer solution (7.5 in pH, 43 ml) and $NaN_3$ (21 mg) to obtain a solution. Actinase E (43 mg) was added to the solution, and the mixture was allowed to stand for 24 hours while being checked for pH every 12 hours. Actinase E (21.5 mg) was added to the reaction mixture again 24 hours later, followed by a reaction again for about 48 hours while being checked for pH. After the termination of the reaction was confirmed by TLC, the reaction mixture was filtered with Celite, and the filtrate was concentrated and purified by gel filtration column chromatography (Sephadex G-25, 2.5×100 cm, $H_2O$). The fractions containing the desired saccharides were collected, concentrated and then freeze-dried.

(c) The residue (about 120 mg) obtained was dissolved in 1.5 ml of water, and 26 mg of sodium bicarbonate was added to the solution. To the mixture was added a solution of 68 mg of Fmoc-Osu [N-(9-fluorenylmethyloxycarbonyl)oxysuccinimide] in 2.5 ml of dimethylformamide, and the resulting mixture was reacted at room temperature for 2 hours. After the disappearance of the material was confirmed by TLC (isopropanol:1M aqueous solution of ammonium acetate=3:2), the reaction mixture was concentrated by an evaporator. To the residue were added 15 ml of water and 25 ml of diethyl ether, and the mixture was stirred for 10 minutes, followed by a separation procedure. The aqueous layer was further washed with 15 ml of diethyl ether, and thereafter concentrated and freeze-dried. The product was purified using an ODS column (Wako-Gel 100C18) for gradient elution. The fractions containing oligosaccharides were collected, concentrated and freeze-dried.

(d) The residue was purified by an HPLC fractionating column (YMC-Pack R&D ODS, D-ODS-5-A, 20×250 mm, AN/25 mM AcONH$_4$ buffer=20/80, 7.5 ml/min., wavelength 274 nm). A fraction of main peak eluted about 15 minutes later was collected, then concentrated and desalted on an ODS column. When freeze-dried, the product afforded about 13.3 mg of the desired disialo Fmoc oligosaccharide derivative.

The $^1$H-NMR data as to the compounds is given below.
$^1$H-NMR (400 MHz, D$_2$O, 30° C., HOD=4.81)
8.01 (2H, d, J=7.5 Hz, Fmoc), 7.80 (2H, d, J=7.5 Hz, Fmoc), 7.60 (2H, dd, J=7.5 Hz, Fmoc), 7.53 (2H, dd, J=7.5 Hz, Fmoc), 5.23 (1H, s, Man4-H$_1$), 5.09 (1H, d, J=9.4 Hz, GlcNAc1-H$_1$), 5.04 (1H, s, Man4'-H$_1$), 4.86 (1H, s, Man3-H$_1$), 4.70~4.66 (m, GlcNAc2-H$_1$ GlcNAc5,5'-H$_1$), 4.54 (2H, d, J=7.9 Hz, Gal6,6'-H$_1$), 4.44 (1H, d, FmocCH), 4.34 (1H, bd, Man3-H$_2$), 4.29, (1H, bd, Man4'-H$_2$), 4.20 (1H, bd, Man4-H$_2$), 2.77 (2H, dd, NeuAc7,7'-H$_{3eq}$), 2.80 (1H, bdd, Asn-βCH), 2.62 (1H, bdd, Asn-βCH), 2.14 (18H, s×6, —Ac), 1.80 (2H, dd, NeuAc7,7'-H$_{3ax}$)

EXAMPLE 2

Disialooligosaccharide-Boc Derivative (Undecasaccharide)

Steps (a) and (b) were performed in the same manner as in Example 1.

(c) The residue (about 120 mg) obtained was dissolved in 1 ml of 0.1N NaOH aq. To the solution was added (Boc)$_2$O (4 ml, product of Tokyo Kasei Co., Ltd.), and the mixture was reacted at room temperature for 2 hours. After the disappearance of the material was confirmed by TLC (isopropanol: 1M aqueous solution of ammonium acetate=3:2), 2.5 ml of dichloromethane was added to the reaction mixture for separation. The aqueous layer was further washed with 2.5 ml of dichloromethane and thereafter adjusted to a pH of 7.0 with 40 mM HCl. The aqueous layer was concentrated, and the residue was purified by an ODS column (gradient H$_2$O 100%→H$_2$O/AN=99/1→H$_2$O/AN=95/5→H$_2$O/AN=90/10). The fraction containing the desired disialooligosaccha-

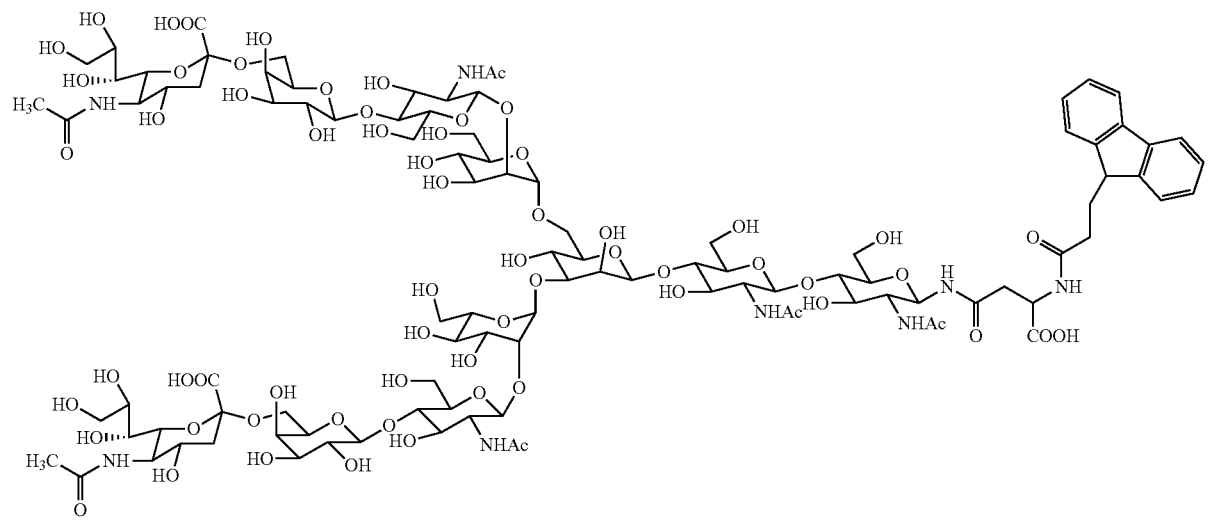

ride Boc derivative (confirmed by HPLC) was collected, concentrated and freeze-dried.

(d) The residue was isolated and purified by HPLC. (YMC-Pack ODS-AM, SH-343-5 AM, 20×250 mm, AN/25 mM AcONH$_4$ buffer=5/95, 7.0 ml/min., wavelength 215 nm). A fraction of main peak eluted about 11 minutes later was collected, concentrated and then desalted by gel column chromatography (Sephadex G-25, H$_2$O). When freeze-dried, the concentrate gave about 10.0 mg of the desired disialooligosaccharide Boc derivative.

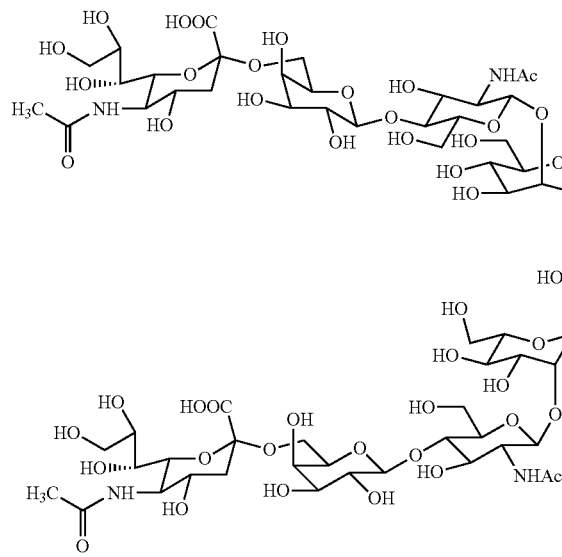
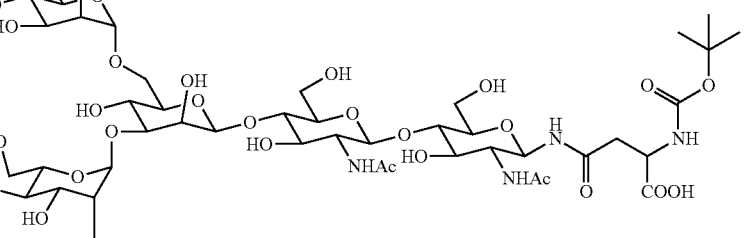

¹H-NMR (400 MHz, D$_2$O, 30° C., HOD=4.81)

δ 5.19 (s, 1H, Man4-H$_1$), 5.12 (d, 1H, J=9.6, GlcNAc1-H$_1$), 5.00 (s, 1H, Man4'-H$_{-1}$), 4.61-4.71 (m, 3H), 4.49 (d, 2H, J=7.6), 4.30-4.40 (bs, 1H, Asn-αCH), 4.31 (s, 1H, Man3-H$_{-2}$), 4.25 (bs, 1H, Man4-H$_{-2}$), 4.17 (bs, 1H, Man4-H$_{-2}$), 2.84 (dd, 1H, Ja=15.6, Jb=4.4, Asn-βCH), 2.72 (dd, 2H, Ja=12.4, Jb=2.8, NeuAc7-H$_{3ex}$), 2.60-2.75 (m, 1H, Asn-βCH), 2.13, 2.12, 2.11 (eachs, 18H, Acx6), 1.77 (dd, 2H, Ja=12.0, Jb=12.4, NeuAc7-H$_{3ax}$), 1.48 (s, 9H, Boc).

EXAMPLE 3

Disialooligosaccharide Ac Derivative
(Undecasaccharide)

The steps (a) and (b) are performed in the same manner as in Example 1.

(c) The residue (about 120 mg) obtained was dissolved in 1 ml of purified water. To the solution were added K$_2$CO$_3$ (72 mg) and then acetic anhydride (99 ml), and the mixture was stirred for about 2 hours. After the mixture was reacted at room temperature for 2 hours, the disappearance of the material was confirmed by TLC (isopropanol:1M aqueous solution of ammonium acetate=3:2), and the 2.5 ml of dichloromethane was added to the reaction mixture for separation. The aqueous layer was further washed with 2.5 ml of dichloromethane and thereafter adjusted to a pH of 7.0 with sat. NaHCO$_3$ aq. The aqueous layer was concentrated and then purified by an ODS column (gradient H$_2$O 100%→H$_2$O/AN=99/1→H$_2$O/AN=95/5). A fraction containing the desired disialooligosaccharide Ac derivative (confirmed by HPLC) was collected and subsequently freeze-dried.

(d) The residue was isolated and purified by HPLC. (YMC-Pack ODS-AM, SH-343-5AM, 20×250 mm, AN/25 mM AcONH$_4$ buffer=1/99, 7.0 ml/min., wavelength 215 nm). A fraction of main peak eluted about 11 minutes later was collected, concentrated and then desalted by gel column chromatography (Sephadex G-25, H$_2$O). When freeze-dried, the concentrate gave about 8.5 mg of the desired disialooligosaccharide Ac derivative.

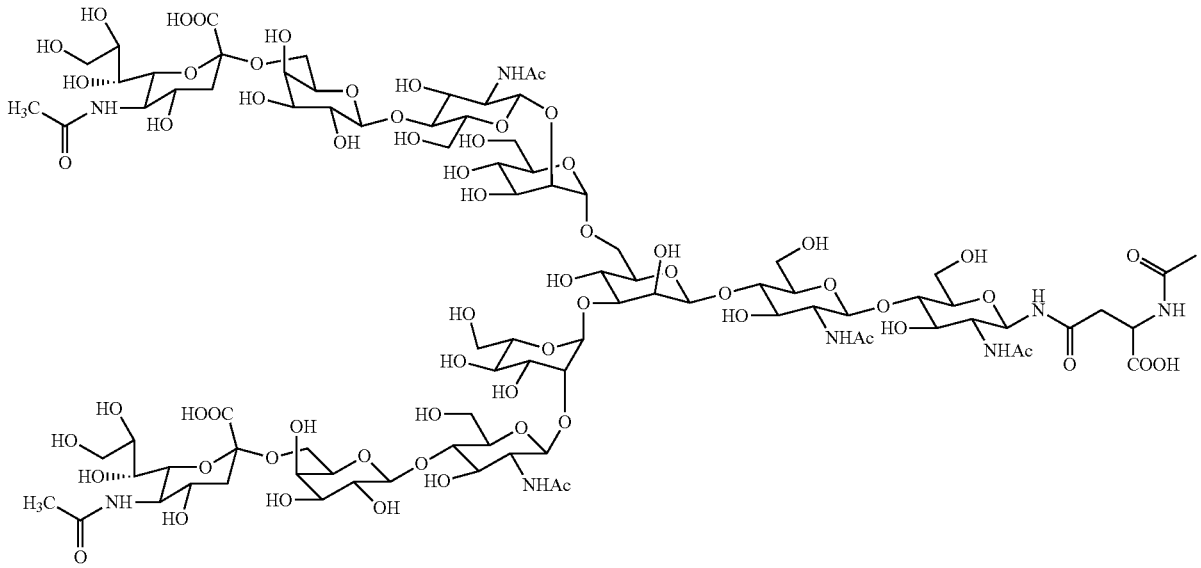

$^1$H-NMR (400 MHz, $D_2O$, 30° C., HOD=4.81)

δ 5.19 (s, 1H, Man4-$H_1$), 5.11 (d, 1H, J=9.6, GlcNAc1-$H_1$), 5.00 (s, 1H, Man4'-$H_{-1}$), 4.66 (bs, 3H), 4.54-4.57 (dd, 1H, Ja=8.1, Jb=4.5), 4.50 (d, 2H, J=7.8), 4.31 (s, 1H, Man3-$H_{-2}$), 4.25 (bs, 1H, Man4-$H_{-2}$), 4.17 (bs, 1H, Man4-$H_{-2}$), 2.85 (dd, 1H, Ja=15.8, Jb=4.3, Asn-βCH), 2.65-2.75 (m, 3H, NeuAc7-$H_{3ex}$, Asn-βCH), 2.13, 2.12, 2.08, 2.06 (eachs, 21H, Ac×7), 1.77 (dd, 2H, Ja=12.1, Jb=12.1, NeuAc7-$H_{3ax}$).

EXAMPLE 4

Disialooligosaccharide-Alloc Derivative (Undecasaccharide)

Steps (a) and (b) were performed in the same manner as in Example 1.

(c) The residue (about 120 mg) obtained was dissolved in 6 ml of 0.1N NaOH aq. To the solution was added $(AllylOCO)_2$O (573 ml, product of Tokyo Kasei Co., Ltd.), and the mixture was reacted at room temperature for 12 hours. After the disappearance of the material was confirmed by TLC (isopropanol: 1M aqueous solution of ammonium acetate=3:2), 12 ml of dichloromethane was added to the reaction mixture for separation. The aqueous layer was further washed with 12 ml of dichloromethane and thereafter adjusted to a pH of 7.0 with 40 mM HCl. The aqueous layer was concentrated, and the residue was purified by an ODS column (gradient $H_2O$ 100%→$H_2O$/AN=99/1→$H_2O$/AN=95/5). The fraction containing the desired disialooligosaccharide Alloc derivative (confirmed by HPLC) was collected, concentrated and freeze-dried.

(d) The residue was isolated and purified by HPLC. (YMC-Pack ODS-AM, SH-343-5AM, 20×250 mm, AN/25 mM $AcONH_4$ buffer=2/98, 7.5 ml/min., wavelength 215 nm). A fraction of main peak eluted about 18 minutes later was collected, concentrated and then desalted by gel column chromatography (Sephadex G-25, $H_2O$). When lyophilized, the concentrate gave about 8.7 mg of the desired disialooligosaccharide Alloc derivative.

$^1$H-NMR (400 MHz, $D_2O$, 30° C., HOD=4.81)

δ 6.01 (ddd, 1H, Ja=17.2, Jb=10.4, Jc=5.2, —$CH_2$—CH=$CH_2$), 5.37 (d, 1H, J=17.2, —$CH_2$—CH=$CH_2$), 5.30 (dd, 1H, Ja=10.4, Jb=1.6, —$CH_2$—CH=$CH_2$), 5.19 (s, 1H, Man4-$H_1$), 5.12 (d, 1H, J=9.6, GlcNAc1-$H_1$), 5.00 (s, 1H, Man4'-$H_{-1}$), 4.60-4.71 (m), 4.50 (d, 2H, J=7.6), 4.35-4.45 (bm, 1H, Asn-αCH), 4.31 (s, 1H, Man3-$H_{-2}$), 4.25 (d, 1H, J=2.0, Man4-$H_{-2}$), 4.17 (d, 1H, J=2.4, Man4-$H_{-2}$), 2.87 (dd, 1H, Ja=15.6, Jb=4.0, Asn-βCH), 2.72 (bdd, 2H, Ja=12.4, Jb=2.4, NeuAc7-$H_{3ex}$), 2.64 (dd, 1H, Ja=15.6, Jb=10.0, Asn-βCH), 2.13, 2.12, 2.11, 2.08, 2.05 (eachs, 18H, Ac×6), 1.77 (dd, 2H, Ja=12.4, Jb=12.0, NeuAc7-$H_{3ax}$), 1.48 (s, 9H, Boc).

INDUSTRIAL APPLICABILITY

The present invention can provide various isolated asparagine-linked oligosaccharide derivatives in larger quantities and with much greater ease than conventionally for use in the field of developing pharmaceuticals or the like.

The invention claimed is:

1. A process for preparing asparagine-linked oligosaccharide derivatives, comprising the steps of:
    (a) treating a delipidated egg yolk with orientase in a solution to obtain a mixture containing peptide-linked oligosaccharides from said egg yolk;
    (b) subjecting the mixture obtained in step (a) to gel filtration column chromatography to isolate the peptide-linked oligosaccharides from the mixture;
    (c) treating the peptide-linked oligosaccharides isolated in step (b) with actinase in a solution to obtain a mixture containing asparagine-linked oligosaccharides; and
    (d) subjecting the mixture obtained in step (c) to gel filtration column chromatography to isolate the asparagine-linked oligosaccharides from the mixture, and introducing a lipophilic protective group to the isolated asparagine-linked oligosaccharides by adding a solution containing the lipophilic protective group to said oligosaccharides to prepare asparagine-linked oligosaccharide derivatives.

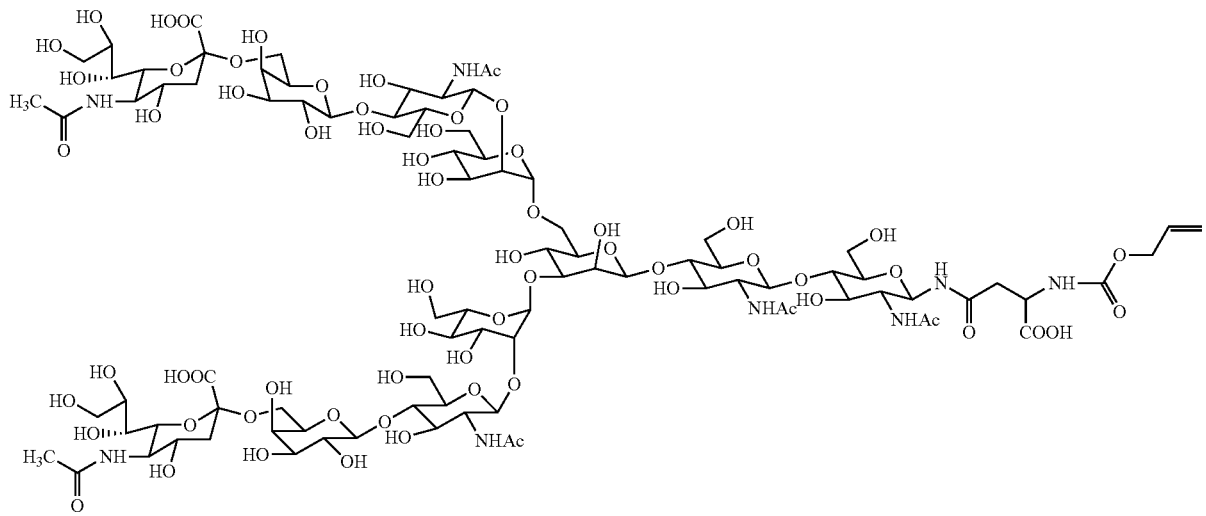

2. The process of claim 1, further comprising the step of:
(e) subjecting the asparagine-linked oligosaccharide derivatives obtained in step (d) to a fractionating chromatography using a reverse phase column and separating each asparagine-linked oligosaccharide derivative from the column.

3. The process of claim 1, wherein the asparagine-linked oligosaccharide derivatives are asparagine-linked undeca- to penta-saccharide derivatives.

4. The process of claim 3, wherein the asparagine-linked oligosaccharide derivatives are asparagine-linked undeca- to hepta-saccharide derivatives.

5. The process of claim 4, wherein the asparagine-linked oligosaccharide derivatives are asparagine-linked undeca- to nona-saccharide derivatives.

6. The process of claim 5, wherein the asparagine-linked oligosaccharide derivatives are asparagine-linked undecasaccharide derivates.

7. The process of claim 6, wherein the asparagine-linked oligosaccharide derivatives have the following formula:

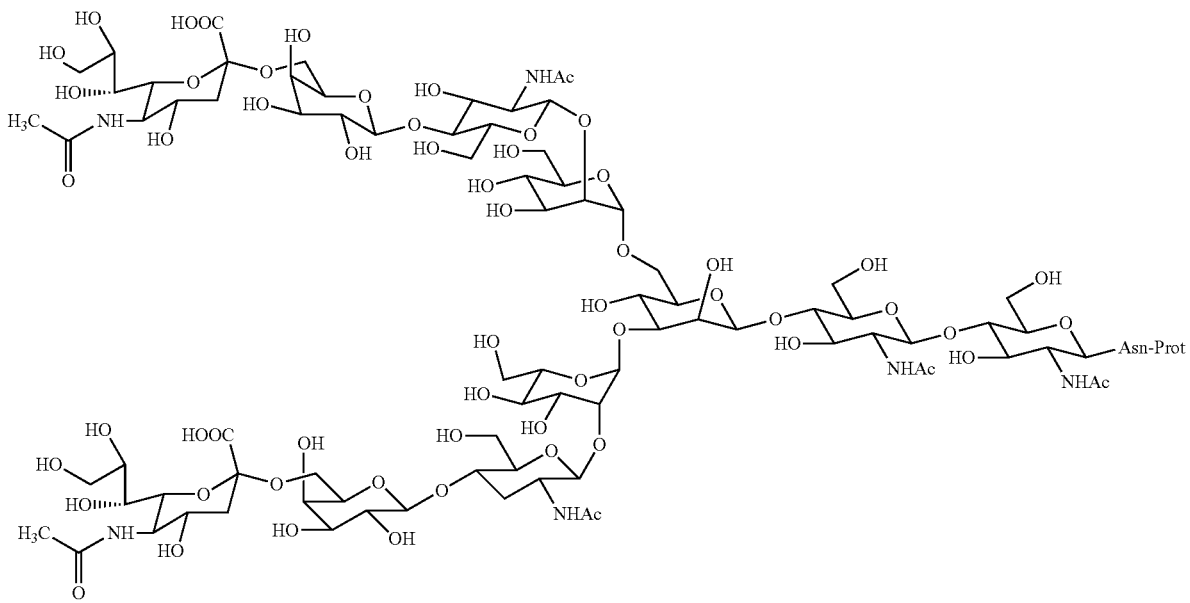

wherein Prot is a lipophilic protective group, Asn is an asparagine, and Ac is an acetyl group.

* * * * *